US006927203B1

(12) United States Patent  (10) Patent No.: US 6,927,203 B1
Kinch et al.  (45) Date of Patent: Aug. 9, 2005

(54) TREATMENT OF METASTATIC DISEASE

(75) Inventors: Michael S. Kinch, Laytonsville, MD (US); Nicole D. Zantek, Silver Springs, MD (US); Patrick W. Hein, Chesterfield, MO (US)

(73) Assignee: Purdue Research Foundation, West Lafayette, IN (US)

( * ) Notice: Subject to any disclaimer, the term of this patent is extended or adjusted under 35 U.S.C. 154(b) by 72 days.

(21) Appl. No.: 09/640,935

(22) Filed: Aug. 17, 2000

Related U.S. Application Data

(60) Provisional application No. 60/149,258, filed on Aug. 17, 1999.

(51) Int. Cl.$^7$ .................. A61K 38/00; A61K 39/395
(52) U.S. Cl. .................. 514/2; 424/130.1; 424/134.1; 424/138.1; 424/141.1
(58) Field of Search ................ 512/2; 424/134.1, 424/138.1, 198.1, 178.1, 141.1, 142.1, 143.1, 145.1, 130.1

(56) References Cited

U.S. PATENT DOCUMENTS

| | | | |
|---|---|---|---|
| 4,472,371 | A | 9/1984 | Burchiel et al. |
| 4,704,692 | A | 11/1987 | Ladner |
| 4,816,567 | A | 3/1989 | Cabilly et al. |
| 5,001,225 | A | 3/1991 | Taylor |
| 5,457,048 | A | 10/1995 | Pasquale et al. |
| 5,514,554 | A | 5/1996 | Bacus |
| 5,585,089 | A | 12/1996 | Queen et al. |
| 5,770,195 | A | 6/1998 | Hudziak et al. |
| 5,811,098 | A | 9/1998 | Plowman et al. |
| 5,824,303 | A | 10/1998 | Bartley et al. |
| 5,872,223 | A | 2/1999 | Uckun |
| 5,876,949 | A | 3/1999 | Dreyfuss et al. |
| 5,981,245 | A | 11/1999 | Fox et al. |
| 2001/0031252 | A1 | 10/2001 | Low et al. |
| 2004/0028685 | A1 | 2/2004 | Kinch et al. |
| 2004/0091486 | A1 | 5/2004 | Kinch et al. |

FOREIGN PATENT DOCUMENTS

| | | |
|---|---|---|
| WO | WO 93/00425 | 1/1993 |
| WO | WO 94/04679 | 3/1994 |
| WO | WO 94/29348 | 12/1994 |
| WO | WO 95/15375 | 6/1995 |
| WO | WO 98/43960 | 10/1998 |
| WO | WO 00/30673 | 6/2000 |
| WO | WO 00/37500 | 6/2000 |
| WO | WO 01/12172 A1 | 2/2001 |
| WO | WO 01/12840 A2 | 2/2001 |
| WO | WO 01/47892 | 7/2001 |
| WO | WO 03/099313 A1 | 12/2003 |
| WO | WO 2004/014292 A2 | 2/2004 |
| WO | WO 94/11020 | 5/2004 |

OTHER PUBLICATIONS

Hill (The Basic Science of Oncology, Tannock et al., Eds, McGraw–Hill, NY, 1992, pp 178–195).*
Hartwell et al (Science, 1997, 278:1064–1068.*
Freshney (Culture of Animal Cells, A Manual of Basic Technique, Alan R. Liss, Inc., 1983, New York, p. 4).*
Dermer (Bio/Technology, 1994, 12:320).*
Lazar et al (Molecular and Cellular Biology, 1988, 8:1247–1252).*
Bowie et al (Science, 1990, 247:1306–1310).*
Burgess et al (J of Cell Bio. 111:2129–2138, 1990).*
On–line Medical Dictionary, Published at the Dept. of Medical Oncology, University of Newcastle upon Tyne Published on Nov. 18, 1997, [retrieved on Jul. 31, 2002] Retrieved from the Internet: <http://www.medical–dictionary.com.*
Gura (Science, 1997, 278:1041–1042).*
Jain (Sci. Am., 1994, 271:58–65).*
Curti (Crit. Rev. in Oncology/Hematology, 1993, 14:29–39).*
Becker et al. "Characterization of the SEK–1 receptor tyrosine kinase" *FEBS Letters* 1995;368(2):353–357.
Chen et al. Abstract. "An enhancer element in the EPhA2 (Eck) gene sufficient for rhombomere–specific expression is activated by HOXA1 and HOXB1 homeobox proteins." *J Biol Chem.* 1998;273(38):24670–5.
Easty et al. "Loss of Expression of Receptor Tyrosine Kinase Family Genes PTKT and SEK in Metastatic Melanoma" *Int. J. Cancer* 1997;71:1061–1065.
Fox et al. "cDNA cloning and tissue distribution of five human Eph–like receptor protein tyrosine kinases" *Oncogene* 1995; 10(5):897–905.
Kerr et al., ed. *LabFax Immunochemistry* 1994; 115, 157, 191–197.
Larrick et al. (In: Human Hybridomas and Monoclonal Antibodies, Engleman and Foung, Eds. 1985, 8–9).
Martone et al. "Immunolocalization of the receptor tyrosine kinase EphA4 in the adult rat central nervous system" *Brain Res.* 1997;771(2):238–250.
McBride et al. "Ephrin–A1 is expressed at sites of vascular development in the mouse," *Mech. Dev.* 1998;77(2):201–204. Abstract only.

(Continued)

Primary Examiner—Larry R. Helms
Assistant Examiner—Misook Yu
(74) Attorney, Agent, or Firm—Mueting, Raasch & Gebhardt P.A.

(57) ABSTRACT

The present invention is directed to compounds and methods for the treatment of metastatic disease. The compounds of this invention have specificity for EphA2, an epithelial cell tyrosine kinase that is overexpressed in metastatic tumor cells. The compounds used in accordance with this invention may be provided in a pharmaceutical composition for treatment of metastatic disease.

46 Claims, 2 Drawing Sheets

OTHER PUBLICATIONS

Muhlbauer et al. Abstract. "Detection of melanoma cells in the blood of melanoma patients by melanoma–inhibitory activity (MIA) reverse transcription–PCR" *Clinical Cancer Research* 1999;5(5):1099–1105.

Ohta et al. The receptor tyrosine kinase, Cek8, is transiently expressed on subtypes of motoneurons in the spinal cord during development *Mechanisms Devel.* 1996;54(1):59–69.

Scully et al. "Isolation and characterization of Desk, a Drosophila eph receptor protein tyrosine kinase," *Mol Cell. Neuro.* 1999;13(5):337–347.

Wada et al. "Glycosylphosphatidylinositol–anchored cell surface proteins regulate position–specific cell affinity in the limb bud" *Devel. Biol.* 1998;202(2):244–252.

Aasheim et al. "A splice variant of human ephrin–A4 encodes a soluble molecule that is secreted by activated human B lymphocytes," *Blood.* 2000;95(1):221–30.

Abrahmsen et al., "Engineering Subtilisin and Its Substrates for Efficient Ligation of Peptide Bonds in Aqueous Solution," *Biochemistry*, 1991;30:4151–4159.

Andres et al., "Expression of two novel eph–related receptor protein tyrosine kinases in mammary gland development and carcinogenesis," *Oncogene,* 1994; 9:1463–1467.

Angrist et al. Chromosomal Localization of the Mouse Src–like Adapter Protein (Slap) Gene and Its putative Human Homolog SLA, *Genomics,* 1995;30:623–625.

Baggiolini et al., "Interleukin–8, a chemotactic and inflammatory cytokine," *FEBS Lett.,* 1992; 307(1):97–101.

Baggliolini et al. "Interleukin–8 and the Chemokine Family" *Int. J. Immunopharmae* 1995; 17(2):103–108.

Behrens et al., "Cell–cell adhesion in invasion and metastasis of carcinomas," *Cancer Treat. Res.,* 1994; 71:251–266.

Biervert et al. "Semiquantitative expression analysis of ephrine–receptor tyrosine kinase mRNA's in a rat model of traumatic brain injury." *Neurosci Lett.* 2001; 315(1–2):25–8.

Blanco et al. "Expression of EphA receptors and ligands during chick cerebellar development." *Mech. Dev.* 2002;114(1–2):225–9.

Bodansky et al., Ed., *Principles of Peptide Synthesis,* Springer–Verlag Inc., NY, 1993, Cover pg., Publication pg., and Table of Contents.

Boerner et al. "Production of antigen–Specific Human Monoclonal Antibodies from in vitro–primed Human Splenocytes", *J. Immunol.,* 1991; 147(1):86–95.

Bohme et al. "PCR mediated detection of a new human receptor–tyrosine–kinase, HEK 2." *Oncogene.* 1993;8(10):2857–62.

Bovenkamp et al. "Degenerate PCR–based cloning method for Eph receptors and analysis of their expression in the developing murine central nervous system and vasculature" *DNA Cell Biol.* 2001;20(4):203–13.

Brady–Kalnay et al., "Dynamic Interaction of PTP$\mu$ with Multiple Cadherins In Vivo" *J. Cell. Biol.,* 1998; 141:287–296.

Brantley et al. "Soluble Eph A receptors inhibit tumor angiogenesis and progression in vivo." *Oncogene.* 2002;21(46):7011–26.

Brodeur et al. Mouse–Human Myeloma Partners for the Production of Heterohybridomas, *Monoclonal Antibody Production Techniques and Application* 1987:51–63.

Bruggemann et al., "Designer mice: the production of human antibody repertoires in transgenic animals" *Year Immunol.* 1993; 7:33–40.

Burridge et al., "Focal adhesions: transmembrane junctions between the extracellular matrix and the cytoskeleton," *Annu. Rev. Cell Dev. Biol.,* 1988; 4:487–525.

Burridge et al., "Focal adhesions, contractility, and signaling," *Annu. Rev. Cell Dev. Biol.,* 1996; 12:463–518.

Carles–Kinch "Antibody Targeting of the EphA2 Tyrosine Kinase Inhibits Malignant Cell Behavior," *Cancer Research* 2002;62:2840–2847.

Carter et al. "EphrinA 1–induced cytoskeletal re–organization requires FAK and p130(cas)." *Nat Cell Biol.* 2002;4(8):565–73.

Carter et al., "Humanization of an anti–p185$^{HER2}$ antibody for human cancer therapy," *Proc. Natl. Acad. Sci. USA,* 1992;89:4285–4289.

Chen et al. "An enhancer element in the EphA2 (Eck) gene sufficient for rhombomere–specific expression is activated by HOXA1 and HOXB1 homeobox proteins." *J Biol Chem.* 1998;273(38):24670–5.

Chen et al. "Germ–line inactivation of the murine Eck receptor tyrosine kinase by gene trap retroviral insertion." *Oncogene* 1996;12(5):979–88.

Chen et al., "Integrin–mediated cell adhesion activates mitogen–activated protein kinases," *J. Biol. Chem.,* 1994;269:26002–26005.

Cheng et al. "Blockade of EphA Receptor Tyrosine Kinase Activation Inhibits Vascular Endothelial Cell Growth Factor–Induced Angiogenesis." *Mol Cancer Res.* 2002;1(1):2–11.

Chothia et al., "Canonical Structures for the Hypervariable Regions of Immunoglobulins," *J. Mol. Biol.,* 1987;196:901–917.

Clark et al. "Aberrant function of the Ras signal transduction pathway in human breast cancer" *Breast Cancer Res. Treat.* 1995;35(1):133–144.

Clark et al., "The Ras–related protein Fheb is farnesylated and antagonizes Ras signaling and transformation," *J. Biol. Chem.,* 1997; 272:10608–10615.

Clark–Lewis et al. Chemical Synthesis, Purification, and Characterization of Two Inflammatory Proteins, Neutrophil Activating Peptide 1 (Interleukin–8) and Neutrophil Activating Peptide 2, *Biochemistry* 1991;30:3128–3135.

Clark–Lewis et al. Structural Requirements for Interleukin–8 Function Identified by Design of Analogs and CXC Chemokine Hybrids, *J. Biol. Chem,* 1994;269:16075–16081.

Cole et al., Monoclonal Antibodies and Cancer Therapy, Alan R. Liss, 1985, p. 77.

Connor et al. "Expression and tyrosine phosphorylation of Eph receptors suggest multiple mechanisms in patterning of the visual system." *Dev Biol.* 1998;193(1):21–35.

D'Amico "Predicting the Sites of Metastasis Form Lung Cancer Using Molecular Biologic Markets" *Ann. Thorac. Surg.* 2001;72:1144–8.

Dawson et al., "Synthesis of Proteins by Native Chemical Ligation," *Science,* 1994;266:776–779.

deLisle et al., *Techniques in Protein Chemistry IV,* Academic Press, New York, 1992, pp. 257–267.

Dohn et al. "Receptor tyrosine kinase EphA2 is regulated by p53–family proteins and induces apoptosis." *Oncogene.* 2001; 20(45):6503–15.

Easty et al., "Novel and Known Protein Tyrosine Kinases and Their Abnormal Expression in Human Melanoma," *J. of Investigative Dermatology,* 1993;101:679–684.

Easty et a., "Protein B61 as a New Growth Factor: Expression of B61 and Up–Regulation of Its Receptor Epithelial Cell Kinase during Melanoma Progression," *Cancer Research,* 1995;55:2528–2532.

Easty et al., "Protein tyrosine kinases in malignant melanoma," *Melanoma Research,* 2000;10:401–411.

Easty et al. "Up–regulation of ephrin–A1 during melanoma progression." *Int J Cancer.* 1999;84(5):494–501.

Fenrick "TEL, a Putative Tumor Suppressor, Modulates Cell Growth and Cell Morphology of Ras–Transformed Cells While Repressing the Transcription of *stromelysin–1*" Molecular and Cellular Biology 2000;20(6):5828–5839.

Ferrone et al, eds., *Handbook of Monoclonal Antibodies,* Noges Publications, Park Ridge, N.J., 1985. Chapter 22 and 303–357.

Foulkes et al. Purification and characterization of a protein–tyrosine kinase encoded by the Abelson murine leukemia virus *J. Biol. Chem.* 1985; 260:8070–8077.

Gale et al., "Eph receptors and ligands comprise two major specificity subclasses and are reciprocally compartmentalized during embryogenesis," *Neuron,* 1996;17:9–19.

Ganju et al. "The Eck receptor tyrosine kinase is implicated in pattern formation during gastrulation, hindbrain segmentation and limb development." *Oncogene,* 1994;9(6):1613–24.

Geiger et al., "Cadherins," *Annu. Rev. Cell Biol.,* 1992;8:307–332.

George et al., "The VAB–1 Eph receptor tyrosine kinase functions in neural and epithelial morphogenesis in C. Elegans," *Cell,* 1998; 92:633–643.

Genzyme–Techne Corporation, Recombinant Mouse Ephrin–A1/Fc, Catalog No. 3602, Mar. 11, 2003.

Grant, *Synthetic Peptides: A User Guide,* W.H. Freeman and Co., N.Y., 1992, Cover pg., Publication pg., and Table of Contents only.

Goding, *Monoclonal Antibodies: Principles and Practice, Academic Press,* 1986, pp. 59–103.

Gussow et al. "Humanization of monoclonal antibodies" *Methods Enzymol.* 1991;203:99–121.

Harlow et al., *Antibodies, A Laboratory Manual,* Cold Spring Harbor Publications, New York, 1988.

Hein, "Regulation of Cell Signaling Induced by the Cell Adhesion Molecule, E–Cadherin," Ph.D. Thesis, Purdue University; 94 pgs., Cover Date Aug. 1999.

Helbling et al. "Requirement for EphA receptor signaling in the segregation of Xenopus third and fourth arch neural crest cells." *Mech. Dev.* 1998;78(1–2):63–79.

Henkeneyer et al., "Nuk controls pathfinding of commissural axons in the mammalian central nervous system," *Cell,* 1996; 86:35–46.

Hess et al., "Molecular regulation of tumor cell vasculogenic mimicry by tyrosine phosphorylation: Role of epithelial cell kinase (ECK/EphA2)," *Cancer Res.,* 2001; 61–3250–3255.

Hoogenboom et al., "By–passing Immunisation Human Antibodies from Syntheti Repertoires of Germline $V_H$ Gene Segments Rearranged in Vitro" *J. Mol. Biol.,* 1991;227:381–388.

Hunter et al. "Novel receptor protein–tyrosine kinases" *Adv Second Messenger Phosphoprotein Res.* 1990;24:260–5.

Hunter et al. "Receptor protein tyrosine kinases and phosphatases." Cold Spring Harb Symp Quant Biol. 1992;57:25–41.

Hutchcroft, "B lymphocyte activation is accompanied by phosphorylation of a 72–kDa protein–tyrosine kinase," *J. Biol. Chem.,* 1991;266:2595–14849.

Jakobovits et al., "Analysis of homozygous mutant chemeric mice: Delection of the immunoglobulin heav–chain joining region blocks B–cell development and antibody production" *Proc. Natl. Acad. Sci. USA,* 1993; 90:2551–2555.

Jakobovits et al., "Germ–like transmission and expression of a humid–derived yeast artificial chromosome" *Nature,* 1993;362:255–258.

Jones, "Replacing the complementarity–determining regions in a human antibody with those from a mouse" *Nature* 1986;321;522–525.

Kabat et al., "Sequences of Proteins of Immunolopgical Interest," *National Institutes of Health,* Bethesda, Md. 1987.

Karam et al. "EphA4 is not required for Purkinje cell compartmentation. Brain Res Dev Brain Res." 2002;135(1–2):29–38.

Kahn et al. "Immunohistochemical Localization of Epidermal and Mallory Body Cytokeratin in Undifferentiated Epithelial Tumors" *American Journal of Clinical Pathology* 1984;84:184–191.

Khosravi–Far et al. "Activation of Rac1, RhoA, and Mitogen–Activated Protein Kinases Is Required for Ras Transformation," *Molecular and Cellular Biology* 1995;15(1)6443–6453.

Kikawa et al. "Regulation of the EphA2 kinase by the low molecular weight tyrosine phosphatase induces transformation." *J. Biol Chem.* 2002;277(42):39274–9.

Kinch et al., "Altered adhesions in ras–transformed breast epitheilal cells," *Biochem. Soc. Trans.,* 1995;23:446–450.

Kinch et al., "Analysis of cell migration," *Cytometry,* Darzynkiewicz et al., Eds., $3^{rd}$ Ed., Academic Press, San Diego, CA, 2000.

Kinch et al., "Cell adhesion mediated by CD4 and MHC class II proteins requires active cellular processes," *J. Immunol.,* 1993; 151:4552–4561.

Kinch et al., "Cytometric analysis of cell contact and adhesion," *Cytometry,* Darzynkiewicz et al., Eds., $3^{rd}$ Ed. Academic Press, San Diego, CA, 2000.

Kinch et al. "E–cadherin engagement stimulates tyrosine phosphorylation" *Cell Adhes. Commun.* 1997;4:425–437.

Kinch et al. "Overexpression and functional alterations of the EphA2 tyrosine kinase in cancer" *Clinical & Experimental Metastasis* 2003;20:59–68.

Kinch et al "Predictive Value of the EphA2 Receptor Tyrosine Kinase in Lung Cancer Recurrence and Survival" *Clin Cancer Res.* 2003;9(2):613–8.

Kinch et al., "The Protein tyrosine kinase $p56^{lck}$ regulates cell adhesion mediated by CD4 and MHC class II proteins," *J. Exp. Med.,* 1994; 180:1729–1739.

Kirk et al., "The human anti–porcine cell mediated response: In vitro studies of function and molecular interaction," *Transplant,* 1993; 55(4):924–931.

Kohler et al. "Continuous culture of fused cells secreting antibody of predefined specificity" *Nature* 1975;256:495–497.

Koolpe et al. "An ephrin mimetic peptide that selectively targets the EphA2 receptor." *J Biol Chem.* 2002;277(49):46974–9.

Kozbor et al., "A Human Hybrid Myeloma for Production of Human Monoclonal Antibodies," *J. Immunol.,* 1984; 133:3001–3005.

Kratchmarova et al. "Characterization of promoter region and genomic structure of the murine and human genes encoding Src like adapter protein." *Gene.* 2001; 262(1–2):267–73.

Lai et al. "Expression of Eph receptors in skeletal muscle and their localization at the neuromuscular junction." *Mol Cell Neurosci.* 2001; 17(6):1034–47.

Lickliter et al. "Embryonic stem cells express multiple Eph–subfamily receptor tyrosine kinases." *Proc Natl Acad Sci U S A.* 1996;93(1):145–50.

Marks et al. "By-passing immunization. Human antibodies from V-gene libraries displayed on phage." *J Mol Biol.* 1991;222(3):581–97.

Maru et al., "Overexpression confers an oncogenic potential upon the eph gene," *Oncogene,* 1990;5:445–447.

McBride et al. "Ephrin–A1 is expressed at sites of vascular development in the mouse" *Mech Dev.* 1998; 77(2):201–4. Abstract Only.

McLaughlin "Functional consequences of coincident expression of EphA receptors and ephrin–A ligands." *Neuron.* 1999;22(4):636–9.

Michael et al. "Efficient gene-specific expression of cre recombinase in the mouse embyro by targeted insertion of a novel IRES–Cre cassette into endogenous loci." *Mech. Dev.* 1999; 85(1–2):35–47.

Miller et al., "The engagement of $\beta_1$ integrins on promonocytic cells promotes phosphorylation of Syk and formation of a protein complex containing Lyn and $\beta_1$ integrin," *Eur. J. Immuno.,* 1999;29:1426–1434.

Miyazaki et al. "EphA2 overexpression correlates with poor prognosis in esophageal squamous cell carcinoma." *Int J Cancer.* 2003; 103(5):657–63.

Morrison et al., "Chimeric human antibody molecules: Mouse antigen–binding domains with human constant region domains," *Proc. Natl. Acad. Sci. USA,* 1984;81:6851–6855.

Munson et al., "LIGAND: A Versatile Computerized Approach for Characterization of Ligand–Binding Systems," *Anal. Biochem.,* 1980;107:220–239.

Murphy et al., "Epidermal growth factor gene expression in human breast cancer cells: regulation of expression by progestins," *Cancer Res.,* 1988; 48:4555–4560.

Nakamoto et al. "Diverse roles for the Eph family of receptor tyrosine kinases in carcinogenesis." *Microsc Res Tech.* 2002;59(1):58–67.

Naruse–Nakajima et al. "Involvement of EphA2 in the formation of the tail notochord via interaction with ephrinA1." Mech Dev. 2001;102(1–2):95–105.

NCBI Locus Link search for "B61" performed Nov. 24, 2003. Http://www.mcbi.nlm.nih.gov/LocusLink/list.cgi paper copy present.

New England Biolabs Product Catalog, 1996, p. 164.

Nemoto et al., "Overexpression of Protein Tyrosine Kinases in Human Esphageal Cancer," *Pathobiology,* 1997;65:195–203.

Nishida et al. "Domain–specific olivocerebellar projection regulated by the EphA–ephrin–A interaction" *Development,* 2002;129(24):5647–58.

Nose et al., "Expressed recombinant cadherins medlatd cell sorting in model systems," *Cell,* 1988;54:993–1001.

Nowakowski et al. "Structures of the Cancer–Related Aurora–A, FAK, and EphA2 Protein Kinases from Nano-volume Crystallography." *Structure* 2002;10(12):1659–67.

O'Brien et al., "A mechanism for trabecular meshwork cell retraction: Ethacrynic acid initiates the dephsphorylation of focal adhesion proteins," *Exp. Eye Res.,* 1997;65:471–483.

Ogawa et al. "The ephrin–A1 ligand and its receptor. EphA2, are expressed during tumor neovascularization." *Oncogene.* 2000; 19(52):6043–52. Dec. 7.

Orsulic et al. "Expression of Eph receptors and ephrins is differentially regulated by E–cadherin." *J Cell Sci.* 2000; 113(Pt 10):1793–802.

Oslo et al., *Remington's Pharmaceutical Science,* 16$^{th}$ ed., Mack Publishing Co., 1980.

Owens et al., "Overexpression of focal adhesion kinase (p125$^{FAK}$) in invasive human tumors," *Cancer Res.,* 1995;55:2752–2755.

Ozawa et al., "A possible new adhesive site in the cell–adhesion molecule uvomorulin," *Mech. Dev.,* 1991;33:49–56.

Paine et al., "Characterization of epithelial phenotypes in mortal and immortal human breast cells," *Int. J. Cancer,* 1992;50:463–473.

Pandey et al., "Role of B61, the ligand for the Eck receptor tyrosine kinase, in TNF–$\alpha$–induced angiogeneis," *Science,* 1995: 269:567–569.

Parsons, "Integrin–mediated signaling: regulation by protein tyrosine kinases and small GTP–binding proteins," *Curr. Opin. Cell Biol.,* 1996;8:146–152.

Partaca "Protein Phosphorylation and Dephosphorylation in Physiologic and Oncologic Processes", *Critical Reviews™ in Oncogenesis,* 1996;7:343–432.

Potla et al. "Reduced expression of EphrinA1 (EFNA1) inhibits three–dimensional growth of HT29 colon carcinoma cells." *Cancer Lett.* 2002;175(2):187–95.

Pratt et al. "Activation of the EphA2 tyrosine kinase stimulates the MAP/ERK kinase signaling cascade" *Oncogene.* 2002;21(50):7690–9.

Presta "Antibody engineering" *Current Op. Struct. Biol.* 1992;2:593–596.

R&D Systems, "Recombinant Mouse Ephrin–A1/Fc Chimera" Catalog No.: 602–A1. Apr. 30, 2002.

Rajarthnam et al., "H NMR Studies of Interleukin 8 Analogs: Characterization of the Domains Essential for Functions", *Biochemistry,* 1944; 33:6623–30.

Riechmann et al., "Reshaping human antibodies for therapy," *Nature,* 1988; 332:323–327.

Rudikoff et al. "Single amino acid substitution altering antigen–binding specificity." *Proc Natl Acad Sci U S A.* 1982;79(6):1979–83.

Ruiz et al. "The expression of the receptor–protein tyrosine kinase gene, eck, is highly restricted during early mouse development." *Mech. Dev.* 1994;46(2):87–100.

Schnolzer et al., "Constructing Proteins by Dovetailing Unprotected Synthetic Peptides: Backbone–Engineered HIV Protease," *Science,* 1992;256:221–225.

Sims et al. "A Humanized CD18 Antibody Can Bock Function without Cell Destruction"0 *J. Immunol.* 1993;151:2296.

Sliwkowski et al., "Nonclinical Studies Addressing the Mechanism of Action of Trastuzumab (Herceptin)" *Seminars in Oncology,* 1999 26:60–70.

Smith et al. "Cardiac Glycoside–Specific Antibodies in the Treatment of Digitalis Intoxication" *Antibodies in Human Diagnosis and Therapy* 1977:365–389.

Southern et al., "Transformation of mammalian cells to antibiotic resistance with a bacterial gene under control of the SV40 early region promoter," *J. Mol. Appl. Genet.*, 1982;1:327–341.

Stearns et al., "Human xenograft models for prostate cancer," The Prostate, 1998; 36:56–58.

Stein et al. "Eph receptors discriminate specific ligand oligomers to determine alternative signaling complexes, attachment, and assembly responses." *Genes Dev.* Mar. 1, 1998; 12(5):667–78.

Stein et al. Nck recruitment to Eh receptor, EphB1/ELK couples ligand activation to c–JUN kinase, *J. Biol. Chem.* 1998;273:1303–1308.

Studer et al. "Genetic interactions between Hoxa1 and Hoxb1 reveal new roles in regulation of early hindbrain patterning." *Development.* 1998;125(6):1025–36.

Straume et al. "Importance of vascular phenotype by basic fibroblast growth factor, and influence of the angiogenic factors basic fibroblast growth factor/fibroblast growth factor receptor–1 and ephrin–A1/EphA2 on melanoma progression." *Am J Pathol.* 2002;160(3):1009–19.

Sulman et al. "ECK, a human EPH–related gene, maps to 1p36.1, a common region of alteration in human cancers." *Genomics* 1997;40(2):371–4.

Verhoeyen et al., "Reshaping Human Antibodies: Grafting an Antilysozyme Activity," *Science,* 1988;239:1534–1536.

Vestweber et al., "Identification of a putative cell adhesion domain of uvomorulin," *EMBO J.*, 1985;4:3393–3398.

Vestweber et al., "Rabbit antiserum against a purified surface glycoprotein decompacts mouse preimplanted embryos and reacts with specific adult tissues," *Exp. Cell Res.*, 1984;152:169–178.

Vestweber et al., "Some structural and functional aspects of the cell adhesion molecule uvomorulin," *Cell Differ.*, 1984;15:269–273.

Vignali et al., "Interactions of CD4 with MHC class II molecules, T cell receptors and p56lck," Phil. Trans. Royal Soc. London, 1993; 342:13–24.

Walker–Daniels et al. "c–Cb1–Dependent EphA2 Protein Degradation Is Induced by Ligand Binding" *Mol Cancer Res.* 2002 1(1):79–87.

Walker–Daniels et al., "The Mechanism of EphA2 Protein Degradation: Implications of Increased EphA2 Protein Levels in Metastatic Cancer Cells," *Proceedings of the American Association for Cancer Research Annual Meeting,* 2001;42:840.

Wang et al. "Negative regulation of EphA2 receptor by Cbl." *Biochem Biophys Res Commun.* 2002;296(1):214–20.

Wendling et al. "Retinoid signaling is essential for patterning the endoderm of the third and fourth pharyngeal arches." *Development.* 2000;127(8):1553–62.

Zantek, "Regulation of EphA2 and Focal Adhesion Kinase in Breast Cancer," Ph.D. thesis, Purdue University; 136 pages. cover dated May 1999.

Zantek et al. "MCF–10A–NeoST: A New Cell System for Studying Cell–ECM and Cell–Cell Interactions in Breast Cancer" *Clinical Cancer Research* 2001;7:3640–3648.

Zelinski et al. "Estrogen and Myc Negatively Regulate Expression of the EphA2 Tyrosine Kinase" *Journal of Cellular Biology* 2002;85:714–720.

Zhang et al., "Relative malignant potential of human breast cancer carcinoma cell lines established from pleural effusions and a brain metastasis," *Invasion Metastasis,* 1991; 11:204–215.

Zhong et al., "Rho–stimulated contractility contributes to the fibroblastic phenotype of ras–transformed epithelial cells," *Mol. Biol. Cell.,* 1997; 8:2329–2344.

Zisch et al., "Complex formation between EphB2 and Src requires phosphorylation of tyrosine 611 in the EphB2 juxtamembrane region," *Oncogene,* 1998;16:2657–2670.

Zoller et al., "Oligonucleotide–directed mutagenesis using M13–derived vectors: an efficient and general procedure for the production of point mutations in any fragment of DNA," *Nucl. Acids Res.,* 1982; 10:6487–6500.

Zelinski et al., "EphA2 Overexpression Causes Tumorigenesis of Mammary Epithelial Cells", *Cancer Research* 61:2301–2306 (Mar. 2001).

N. D. Zantek et al., "Identification of an adhesion–associated tyrosine kinase that is tightly regulated in breast cancer," *Mol. Bio. Cell,* 8(Supp):134A, abstract 777 (1997); 37th Annual Meeting of the American Society for Cell Biology, (Dec. 13–17, 1997).

N. D. Zantek et al., "Epithelial cell kinase (ECK/EPHA2) regulation in breast cancer," *Mol. Bio. Cell,* 9(Supp):134a, abstract 773 (1998); 38th Annual Meeting of the American Society for Cell Biology, (Dec. 12–16, 1998).

N. D. Zantek et al., "Regulation of the EphA2 receptor tyrosine kinase by estrogen and myc," *Proceedings of the American Assoc. for Cancer Research Annual, 40*:687, abstract 4537 (1999); 90th Annual Meeting of the American Association for Cancer, (Apr. 10–14, 1999).

J. L. Walker–Daniels, "Overexpression of EphA2 in Metastatic Cancer Cells: A Role for Ras Signaling," *Mol, Bio. Cell, 10,* abstract 2469 (1999); 39$^{th}$ American Society for Cell Biology, (Dec. 11–15, 1999).

N. D. Zantek et al., "Analysis of Cell Migration," *Methods in Cell Biology, 63,* Chapter 25, 549–559 (2001).

P. Agre et al., "The human tumor cloning assay in cancer drug development", *Investigational New Drugs, 1,* 033–045 (1983).

S.–N. Bae et al., "Molecular and cellular analysis of basement membrane invasion by human breast cancer cells in Matrigel–based in vitro assays," *Breast Cancer Res. Treat., 24,* 241–255 (1993).

T. D. Bartley et al., "B61 is a ligand for the ECK receptor protein–tyrosine kinase," *Nature, 368,* 558–560 (1994).

J. Baselga et al., "Recombinant Humanized Anti–HER2 Antibody (Herceptin™) Enhances the Antitumor Activity of Paclitaxel and Doxorubicin against HER2/neu Overexpressing Human Breast Cancer Xenografts," *Cancer Res., 58,* 2825–2831 (1998).

W. Birchmeier, "E–cadherin as a tumor (invasion) suppressor gene", *Bioessays, 17* 97–99 (1995).

J. Bynum et al., "Development of Class–Switched, Affinity–Matured Monoclonal Antibodies Following a 7–Day Immunization Schedule", *Hybridoma, 18* 407–411 (Oct., 1999).

W. G. Cance et al., "Protein kinases in human breast cancer", *Breast Cancer Research and Treatment, 35,* 105–114 (1995).

G. J. Clark et al., "Overexpression of the Ras–related TC21/R–Ras2 protein may contribute to the development of human breast cancers," *Oncogene, 12,* 169–176 (1996).

S. Davis et al., "Ligands for EPH–related receptor tyrosine kinases that require membrane attachment or clustering for activity," *Science, 266,* 816–819 (1994).

V. T. DeVita, Jr., "Principles of Cancer Management: Chemotherapy", *Cancer: Principles and Practice of Oncology, Fifth Edition,* V. T. Devita, Jr. et al., Eds., Lippincott–Raven, Philadelphia, 333–347 (1997).

R. B. Dickson et al., "Growth factors in breast cancer," *Endocrine Rev.,* 16, 559–589 (1995).

D. J. Easty et al., "Abnormal protein tyrosine kinase gene expression during melanoma progression and metastasis," *Intl. J. Cancer,* 60, 129–136 (1995).

Eph Nomenclature Committee, "Unified Nomenclature for Eph Family Receptors and Their Ligands, the Ephrins", *Cell,* 90, 403–404, (1997).

I. J. Fidler, "Molecular Biology of Cancer: Invasion and Metastasis", *In Cancer: Principles and Practice of Oncology,* V. T. Devita et al, eds. (Philadelphia: Lippincott–Raven), p. 135–152 (1997).

S. M. Frisch, "Integrins and anoikis", *Current Opinion in Cell Biology,* 9, 701–706 (1997).

D. W. Fry et al., "Inhibitors of protein tyrosine kinases", *Current Opinion in Biotechnoloigy,* 6, 662–667 (1995).

N.. W. Gale et al., "Ephrins and their receptros: a repulsive topic?", *Cell Tissue Res.,* 290, 227–241 (1997).1

D. Giunciuglio et al., "Invasive phenotype of MCF10A cells overexpressing c–Ha–ras and c–erb–2 oncogenes," *Intl. J. Cancer,* 63, 815–822 (1995).

J. R. Glenney, Jr. et al., "Novel Tyrosine Kinase Substrates from Rous Sarcoma Virus–transformed Cells are Present in the Membrane Skeleton", *The Journal of Cell Biology,* 108, 2401–2408 (1989).

A. W. Hamburger, "The Human Tumor Clonogenic Assay as a Model System in Cell Biology", *International Journal of Cell Cloning,* 5, 89–107 (1987).

D. Hanahan, et al., "The hallmarks of cancer", *Cell,* 100 57–70 (Jan. 7, 2000).

D. E. Henson, "Molecular and genetic targets in early detection", *Current Opinion in Oncology,* 11, 419–425 (1999).

S. J. Holland et al., Cell–contact–dependent signalling in axon growth and guidance: Eph receptor tyrosine kinases and receptor protein tyrosine phosphatase beta. *Curr Opinion Neurobiol.,* 8 117–127 (1998).

R. M. Hudziak et al., "p185$^{HER2}$ Monoclonal Antibody Has Antiproliferative Effects In Vitro and Sensitizes Human Breast Tumor Cells to Tumor Necrosis Factor," *Mol. Cell Biol.,* 9, 1165–1172 (1989).

J. Huai et al., "Investigation of a Possible Receptor Function of Ephrina Ligands", *European Journal of Neuroscience,* 12, 179 (Sep. 2000).

T. Hunter, "Oncoprotein networks", *Cell,* 88 333–346 (1997).

S. B. Kanner et al., "Monoclonal antibodies to individual tyrosine–phosphorylated protein substrates of oncogene–encoded tyrosine kinases", *Proc. Natl. Acad. Sci. USA,* 87, 3328–3332, (May 1990).

P. Keely et al. "Integrins and GTPases in tumour cell growth, motility and invasion", *Trends Cell Biol.,* 8 101–106 (1998).

K. Kilpatrick et al., "Gene Gun Delivered DNA–Based Immunizations Mediate Rapid Production of Murine Monoclonal Antibodies to the Flt–3 Receptor", *Hybridoma,* 17, 569–576 (1998).

K. Kilpatrick et al., "High Affinity Monoclonal Antibodies to PED/PEA–15 Generated Using 5 μg of DNA", *Hybridoma,* 19, 297–302 (Aug. 2000).

K. Kilpatrick et al., "Rapid Development of Affinity Matured Monoclonal Antibodies Using RIMMS," *Hybridoma,* 16, 381–389 (1997).

M. S. Kinch et al., "Identification of Tyrosine Phosphorylated Adhesion Proteins in Human Cancer Cells," *Hybridoma,* 17, 227–235 (1998).

M. S. Kinch et al., "Tyrosine phosphorylation regulates the adhesions of ras–transformed breast epithelia," *J. Cell Biol.,* 130, 461–471 (1995).

B. S. Kondapaka et al., "Tyrosine kinase inhibitor as a novel signal transduction and antiproliferative agent: prostate cancer", *Molecular and Cellular Endocrinology,* 117, 53–58 (1996).

J. A. Lawrence, "Mechanisms of tumor invasion and metastasis", *World J. Urol.,* 14, 124–130 (1996).

A. Levitzki, "Tyrosine Kinase Inhibition: An Approach to Drug Development", *Science,* 267, 1782–1788 (1995).

G. D. Lewis et al., "Differential responses of human tumor cell lines to anti–p185$^{HER2}$ monoclonal antibodies," *Cancer Immunol. Immunother.,* 37, 255–263 (1993).

R. Lindberg et al., "cDNA Cloning and Characterization of Eck, an Epithelial Cell Receptor Protein–tyrosine Kinase in the Eph/elk Family of Protein Kinases," *Mol. Cell Biol.,* 10(12):6316–6324 (Dec. 1990).

R. K. Malik et al., "Integrin–mediated signaling in normal and malignant cells: a role of protein tyrosine kinases", *Biochimica et Biophysica Acta,* 1287, 73–76 (1996).

H. Miao et al., "Activation of Eph2 kinase suppresses integrin function and causes focal–adhesion–kinase dephosphorylation," *Nat. Cell Biol.,* 2(2):62–69 (Feb. 2000).

F. R. Miller et al., "Xenograft model of progressive human proliferative breast disease", *J. Natl. Cancer Instit.,* 85, 1725–1732 (1993).

M. Nakamoto, "Eph receptors and ephrins", *Int'l. J. Biochem. Cell Biol.,* 32, 7–12 (2000).

H. F. Oettgen et al. "The History of Cancer Immunotherapy," in *Biologic Therapy of Cancer,* Devita et al., eds., Lippincott, Philadelphia, Chapter 6, pp. 87–119 (1991).

A. Pandey et al., "Activation of the Eck receptor protein tyrosine kinase stimulates phosphatidylinositol 3–kinase activity," *J. Biol. Chem.,* 269, 30154–30157 (1994).

A. Pandey et al., "Characterization of a novel src–like adapter protein that associates with the Eck receptor tyrosine kinase," *J. Biol. Chem.,* 270, 19201–19204 (1995).

J. T. Parsons et al., "Protein–tyrosine kinases, oncogenes, and cancer", *Important Adv. Oncol.,* 3–17 (1993).

E. B. Pasquale, "The Eph family of receptors," *Current Opinion in Cell Biology,* 9, 608–615 (1997).

R. Patarca "Protein Phosphorylation and Dephosphorylation in Physiologic and Oncologic Processes", *Critical Reviews in Oncogenesis,* 7, 343–432 (1996).

R. J. Pauley et al., "The MCF10 family of spontaneously immortalized human breast epithelial cell lines: models of neoplastic progression", *Eur J. Cancer Prev 2 Suppl, 3* 67–76 (1993).

Pegram et al., Abstract, "Antibody dependent cell–mediated cytotoxicity in breast cancer patients in Phase III clinical trials of a humanized anti–HER2 antibody," *Proc. Am. Assoc. Cancer Res.,* 38, 602 (1997).

M. D. Pegram et al., "HER–2/neu as a predictive marker of response to breast cancer therapy," *Breast Cancer Res. Treat.,* 52, 65–77 (1998).

M. F. Press et al., "HER–2/neu Oncogene Amplification and Expression in Breast and Ovarian Cancers," *Prog. Clin. & Biol. Res., 354A,* 209–221 (1990).

J. E. Price, "Analysing the metastatic phenotype", *J. Cell Biochem., 56,* 16–22 (1994).

J. E. Price, "Metastasis from human breast cancer cell lines", *Breast Cancer Res. Treat., 39* 93–102 (1996).

J. S. Rhim et al., "Human Prostate Carcinogenesis," *Crit. Rev. Oncog., 8,* 305–328 (1997).

S. Roche et al., "Sre–like adaptor protein (SLAP) is a negative regulator of mitogenesis", *Current Biol., 8* 975–978 (1998).

I. M. Rosenberg et al., "Epithelial cell kinase–B61: an autocrine loop modulating intestinal epithelial migration and barrier function," *Am. J. Physiol., 273,* G824–G832 (1997).

S. A. Rosenberg, "Principles of Cancer Management: Surgical Oncology", *Cancer: Principles and Practice of Oncology, Fifth Edition,* V. T. Devita, Jr. et al., Eds, Lippincott–Raven, Philadelphia, cover page, table of contents and 295–333 (1997).

E. Ruoslahti, "Cell adhesion and tumor metastasis", *Princess Takamatsu Symp, 24* 99–105 (1994).

E. Ruoslahti, "Fibronectin and Its Integrin Receptors in Cancer" *Advances in Cancer Research, 76,* 1–20 (1999).

M. F. Sarosdy et al., "Prediction of Response to Cancer Chemotherapy", *Drugs, 26,* 454–459 (1983).

D. D. Schlaepfer et al., "Signal transduction from the extracellular matrix–a role for the focal adhesion protein–tyrosine kinase FAK", *Cell Structure Function, 21* 445–450 (1996).

S. Shak, "Overview of the trastuzmab (Herceptin) anti–HER2 monoclonal antibody clinical program in HER2–overexpressing metastatic breast cancer," *Seminars Oncol., 26,* 71–77 (Aug. 1999).

D. J. Slamon et al., "Studies of the HER–2/neu Proto–oncogene in Human Breast and Ovarian Cancer," *Science, 244,* 707–712 (1989).

P. S. Steeg et al. "Molecular analysis of premalignant and carcinoma in situ lesions of the human breast", *Am J Pathology, 149* 733–738 (1996).

P. van der Geer et al., "Receptor Protein–Tyrosine Kinases And Their Signal Transduction Pathways," *Annu. Rev. Cell Biol., 10,* 251–337 (1994).

H. D. Varmus et al., "Biochemical mechanisms of oncogene activity: proteins encoded by oncogenes", *Cancer Surv., 5* 153–158 (1986).

T. Volberg et al., "The effect of tyrosine–specific protein phosphorylation on the assembly of adherens–type junctions", *EMBO J., 11,* 1733–1742 (1992).

J. Walker–Daniels et al., "Overexpression of the EphA2 Tyrosine Kinase in Prostate Cancer," *Prostate, 41*(4):275–280 (Dec. 1999).

D. J. Waters et al., "Spontaneous Metastasis of PC–3 Cells in Athymic Mice After Implantation in Orthotopic or Ectopic Microenvironments," *Prostate, 26,* 227–234 (1995).

V. M. Weaver et al., "The development of a functionally relevant cell culture model of progressive human breast cancer," *Semin. Cancer Biol., 6,* 175–184 (1995).

L. M. Weiner, "Monoclonal antibody therapy of cancer," *Seminars Oncol., 26,* 43–51 (Oct. 1999).

N. D. Zantek et al., Abstract "Identification of an Adhesion–Associated Tyrosine Kinase that is Tightly Regulated In Breast Cancer," American Society for Cell Biology, (Dec. 15, 1998).

N. D. Zantek et al., "E–Cadherin Regulates the Function of the EphA2 Receptor Tyrosine Kinase," *Cell Growth Differ., 10*(9):629–638 (Sep. 1999).

\* cited by examiner

- Inject Lymph Nodes Every Other Day for 10 Days
- Harvest Lymph Node Cells
- Fuse with Myeloma Overexpressing Bcl-2
- Screen by Immunofluorescence Microscopy
- Select for Antigen with Sites of Cell Adhesion:
    - Cell-Cell or
    - Cell-ECM/Membrane Ruffles

TREATMENT OF METASTATIC DISEASE

This application claims priority under 35 U.S.C. § 119(e) to U.S. Provisional Application No. 60/149,258, filed Aug. 17, 1999, which is expressly incorporated by reference herein.

GOVERNMENT FUNDING

The present invention was made with government support under Grant No. DAMD 17-98-1-8146, awarded by Army Breast Cancer. The Government has certain rights in this invention.

FIELD OF THE INVENTION

The present invention relates to diagnosis and treatment of metastatic disease. More particularly, this invention relates to the use of an epithelial cell tyrosine kinase that is overexpressed in metastatic tumor cells as the target for the diagnosis and treatment of metastatic disease. Most particularly, this invention relates to the use of compounds that interact with and alter expression of the epithelial cell tyrosine kinase.

BACKGROUND AND SUMMARY OF THE INVENTION

Cancer is a disease of aberrant signal transduction. The most dangerous forms of cancer are malignant cells that metastasize to distant sites in a body. Metastatic cells have acquired the ability to break away from the primary tumor, translocate to distant sites, and colonize distant and foreign microenvironments. Cancer cell metastasis requires cellular capacity to 1) detach from a primary tumor, 2) migrate and invade through local tissues, 3) translocate to distant sites in the body (via lymph or blood), 4) colonize a foreign site, and 5) grow and survive in this foreign environment. All of these behaviors are linked to cell adhesions. Cell adhesions control the physical interactions of cells with their microenvironment. Cell adhesions also initiate signals that dictate tumor cell growth, death, and differentiation. At the cellular level, metastatic cells have overcome restraints upon cell growth and migration that result from physical linkages and signals conveyed by cell-cell contacts. Malignant cells often have increased interactions with surrounding extracellular matrix (ECM) proteins that provide linkages and signals that promote several aspects of metastasis.

Levels of protein tyrosine phosphorylation regulate a balance between cell-cell and cell-ECM adhesions in epithelial cells. Elevated tyrosine kinase activity weakens cell-cell contacts and promotes ECM adhesions. Alteration in levels of tyrosine phosphorylation is believed to be important for tumor cell invasiveness. Tyrosine phosphorylation is controlled by cell membrane tyrosine kinases, and increased expression of tyrosine kinases is known to occur in metastatic cancer cells.

EphA2 is a 130 kDa receptor tyrosine kinase that is expressed on adult epithelia. A member of the Eph family of tyrosine kinases known as Ephrins, EphA2 is a transmembrane receptor tyrosine kinase with a cell-bound ligand. EphA2 expression has been found to be altered in many metastatic cells, including lung, breast, colon, and prostate tumors. Additionally, the distribution and/or phosphorylation of EphA2 is altered in metastatic cells. Moreover, cells that have been transformed to overexpress EphA2 demonstrate malignant growth, and stimulation of EphA2 is sufficient to reverse malignant growth and invasiveness. EphA2 is a powerful oncoprotein. The present invention is directed to compounds and methods that target EphA2 for the diagnosis and treatment of metastatic cancers.

One approach to cancer therapy is the administration of preformed antibodies to predetermined tumor antigens. This process is known as passive antibody treatment. An example of passive antibody treatment is the use of Herceptin® for the treatment of breast cancer. Herceptin® is a humanized form of a murine monoclonal antibody specific for the extracellular domain of Her2/Neu. The basis for treatment with Herceptin® is that 25–30% of metastatic breast cancers overexpress the Her2/Neu receptor tyrosine kinase. Herceptin® has been well tolerated in clinical trials and shows much promise for the maintenance and regression of metastatic breast cancer.

Effective passive immunotherapy for treatment of tumors requires isolation and preparation of an antibody that: 1) targets an antigen that is overexpressed in metastatic tumors; 2) targets an extracellular epitope of said antigen; 3) is not cross-reactive with any other antigen in a patient's circulation; and 4) exhibits tumoricidal or tumoristatic activity.

In a preferred embodiment, this invention relates to the selection and use of antibodies that are specific to an extracellular epitope of EphA2. The methods of this invention include the preparation, selection, and use of EphA2 specific antibodies for cancer therapy.

Another approach to cancer treatment is to use agonists to stimulate expression. For example, EphrinA1-$F_c$, the extracellular domain of ephrinA1 linked to immunoglobulin heavy chain, (see Miao, H., et al., EphA2 kinase associates with focal adhesion kinase and upon activation, inhibits integrin-mediated cell adhesion and migration, Nature Cell Biol 2, 62–69 (2000), hereby incorporated by reference) can be used to increase the phosphotyrosine content of EphA2. Thus, in another preferred embodiment, this invention relates to the use of agonists or antagonists to alter the expression of EphA2 in metastatic cells.

Thus, this invention is directed to the use of agonists and antagonists to alter the expression of EphA2. EphA2 may be targeted by use of artificial or hybrid forms of the protein, protein inhibitors, antisense oligonucleotides, or small molecule inhibitors. Also, while a preferred embodiment is directed to use of monoclonal antibodies, polyclonal, artificial, and hybrid antibodies are known in the art. It should be understood that use of techniques known in the art to target EphA2 are within the scope of this invention.

One aspect of this invention is a pharmaceutical composition for the treatment of mammalian metastatic tumors which overexpress EphA2, comprising a compound that specifically interacts with an extracellular epitope of EphA2 in an amount effective to reduce metastatic disease and a pharmaceutically acceptable carrier. In the preferred embodiment, the pharmaceutical composition comprises the antibody B2D6, an antibody that specifically binds to an extracellular epitope of EphA2.

Another aspect of this invention is a method of treating a patient having a metastatic tumor which overexpresses EphA2. The method comprises administering to the patient a therapeutic amount of a compound that binds to an extracellular epitope of EphA2. In a preferred embodiment, the compound is an antibody.

A third aspect of this invention is a method for detecting the presence of metastatic cells. The method includes use of a labeled antibody specific to an extracellular epitope of EphA2. A cell sample is incubated with the antibody, unbound antibody is removed, and the bound labeled antibody is detected.

An additional aspect of this invention is a method for producing antibodies which inhibit metastatic tumor proliferation by specifically binding to an extracellular epitope of EphA2. This method includes injecting tyrosine phosphorylated proteins into the lymph nodes of a mammal, harvesting the lymph nodes, fusing the lymph node cells with myeloma cells to form hybridomas, and selecting hybridomas which produce antibodies specific for EphA2.

In still another aspect of this invention, a pharmaceutical composition for treatment of a mammalian metastatic tumor is provided, the composition comprising a compound that alters expression of EphA2 in an amount effective to reduce metastatic proliferation of said tumor, and a pharmaceutically acceptable carrier therefor. In a preferred embodiment, the composition comprises an ephrin.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 2A is a western blot showing EphA2 expression in various human prostate cancer cell lines;

FIG. 2B is similar to FIG. 2A, except showing EphA2 expression in a human prostatic epithelial cell line and expression in the cell line after transformation by oncogenic K-Ras or X-irradiation;

FIG. 2C is similar to FIG. 2B, except showing EphA2 expression in another human prostatic epithelial cell line and expression in the cell line after transformation by oncogenic K-Ras or X-irradiation;

DETAILED DESCRIPTION OF THE INVENTION

EphA2 is expressed differently in normal and metastatic cells. In normal breast and prostate epithelial cells, EphA2 is enriched in within cites of cell adhesion. Conversely, in metastatic prostate cells EphA2 is diffusely distributed, and in metastatic breast cancer cells EphA2 is redistributed into the membrane ruffles. EphA2 expression is also known to be altered in lung and colon malignancies, and it is believed that EphA2 altered expression occurs in other types of metastases, particularly epithelial malignancies. Thus, techniques designed to alter EphA2 expression can be exploited to diagnose and treat metastatic disease.

In a preferred embodiment, antibodies specific for tyrosine phosphorylated proteins in cancer cells have been isolated and used to target cancer cells in passive immunotherapy. This approach is based upon the fact that many tyrosine kinases, e.g. Her2/Neu, are expressed by oncogenes and are therefore overexpressed in cancer cells. The present invention is directed to the production and use of antibodies capable of recognition of and specific binding to extracellular epitopes of the tyrosine kinase EphA2. The antibodies are produced by selected hybridomas, themselves the product of fusion of myeloma cells with lymph node cells harvested from animals subjected to a specific inoculation protocol designed for increased sensitivity and diversity of responding hybridomas.

Figure 1:
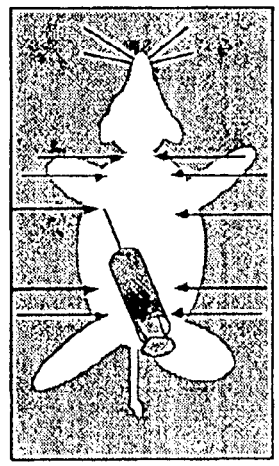
FIG. 1 is an overview of the RIMMS procedure, through which the antibodies of this invention are generated.

To produce these hybridomas, tyrosine phosphorylated proteins from Ras-transformed human epithelial cells were isolated by affinity chromatography using existing phosphotyrosine specific antibodies. The tyrosine phosphorylated proteins are then used as an immunogen for producing monoclonal antibodies according to the procedure illustrated in FIG. 1. Low-dose amounts of tyrosine phosphorylated proteins are injected proximal to lymph nodes of a mammal, every other day, over a ten day period (the RIMMS strategy). B cells from engorged lymph nodes are then isolated and fused with Bcl-2-overexpressing myeloma cells, to minimize apoptosis after fusion. This method results in increased diversity, specificity, and cost-effectiveness of hybridoma production. The hybridomas are screened to identify those hybridomas producing antibodies that distinguish malignant from normal cancer cells.

Hybridomas producing antibodies specific to EphA2 have been selected. Use of the RIMMS technique has resulted in the production of a multiplicity of hybridomas producing monoclonal antibodies that specifically bind EphA2. To date, at least 450 hybridomas have been identified which produce antibodies capable of distinguishing malignant from normal cancer cells. Of the first four such hybridomas to be characterized, two recognize independent epitopes on EphA2. The first, D7, produces an antibody recognizing an intracellular epitope. The second, B2D6, produces an antibody that specifically binds an extracellular epitope of EphA2, a characteristic that enables its effective use for the diagnosis and treatment of selected metastatic tumors. Murine hybridomas B2D6 and D7 were deposited on Dec. 8, 2000, with the American Type Culture Collection, 10801 University Boulevard, Manassas, Va. 20110-2209, and assigned ATCC Numbers PTA-2754 and PTA-2755, respectively.

While the RIMMS strategy has proven to be valuable in the production of EphA2 specific antibodies, other techniques are known in the art for producing antibodies to a specific antigen, and these techniques are within the scope of this invention.

It is known in the art to use antibodies to detect the presence or overexpression of a specific protein. Because EphA2 is overexpressed in metastatic cells, EphA2-specific antibodies of this invention may be used to detect this overexpression and, thus, to detect metastatic disease. Such techniques include but are not limited to western blotting, precipitation, agglutination, and ELISA assays. These techniques are well known in the art. Also, the extracellular epitope specificity of EphA2-specific antibodies of this invention can be exploited to detect changes in EphA2 localization which are associated with metastasis. In normal breast and prostate epithelial cells, EphA2 is enriched in within cites of cell adhesion, whereas in metastatic cells, EphA2 distribution is altered. In metastatic prostate cells EphA2 is diffusely distributed, and in metastatic breast cancer cells EphA2 is redistributed into the membrane ruffles. EphA2 expression is also known to be altered in lung and colon malignancies, and it is believed that EphA2 altered expression occurs in other types of metastasis, particularly epithelial malignancies. Techniques such as immunohistological staining or immunofluorescent microscopy are well known in the art and may be used to visualize EphA2 distribution. See, for example, U.S. Pat. No. 5,514,554, hereby incorporated by reference. In order to detect overexpression or altered distribution of EphA2, the EphA2-specific antibodies may be labeled covalently or non-covalently with any of a number of known detectable labels, such as fluorescent or radioactive substances, as is known in the art. Alternatively, a secondary antibody specific for the antibodies of this invention is labeled with a known detectable label and used to detect the EphA2-specific antibodies in the above techniques. Thus, the antibodies of this invention provide methods to detect metastatic transformation.

The present invention also employs antibodies specific for an extracellular epitope of EphA2 in therapeutic compositions and methods for use. When used for in vivo therapy, a pharmaceutical composition administered to a patient comprises EphA2-specific antibodies in therapeutically effective amounts in a pharmaceutically acceptable carrier. In a preferred embodiment, the EphA2-specific antibodies have been "humanized." Humanized antibodies include "chimeric antibodies" made by splicing genes from a mouse (or other mammal) antibody of appropriate antigen specificity together with genes from a human antibody molecule of appropriate biological activity. Such techniques are known in the art. See, for example, U.S. Pat. No. 5,811,098, hereby incorporated by reference. In addition to antibodies, natural or artificial ligands, peptides, anti-sense, ATP analogues, or other small molecules capable of specifically targeting EphA2 may be employed.

An example of another way to target EphA2 is the use of ephrins to activate or inhibit EphA2. For example, EphrinA1-$F_c$, the extracellular domain of ephrinA1 linked to immunoglobulin heavy chain, increases the phosphotyrosine content of EphA2. EphrinA1-$F_c$ reverses the malignant behavior of EphA2 transformed cells. Thus, another preferred embodiment of this invention is a pharmaceutical composition comprising an ephrin or a hybrid form of ephrin administered in a therapeutic amount.

Therapeutic amounts are amounts which eliminate or reduce the patient's tumor burden, or which prevent or reduce the proliferation of metastatic cells. The dosage will depend on many parameters, including the nature of the tumor, patient history, patient condition, the possible co-use of other oncolytic agents, and methods of administration. Methods of administration include injection (e.g., parenteral, subcutaneous, intravenous, intraperitoneal, etc.) for which the antibodies are provided in a nontoxic pharmaceutically acceptable carrier such as water, saline, Ringer's solution, dextrose solution, 5% human serum albumin, fixed oils, ethyl oleate, or liposomes. Typical dosages may range from about 0.01 to about 20 mg/kg, and more particularly from about 0.1 to about 10 mg/kg. Other methods of administration include oral and transdermal. Acceptable carriers for oral ingestion in accordance with the present invention can be formulated using art-recognized techniques into pharmaceutically acceptable liquid carriers or in combination with pharmaceutically acceptable solid carriers in the form of tablets, capsules, caplets, or gel-seals. Other effective methods of administration and dosages may be determined by routine experimentation and are within the scope of this invention.

Therapeutic methods employing EphA2-specific antibodies may be combined with chemotherapy, surgery, and radiation therapy, depending on type of the tumor, patient condition, other health issues, and a variety of factors. The methods may also include immunoconjugates for targeted immunotoxin-mediated therapy, wherein antibodies of this invention are covalently or non-covalently conjugated to various cytotoxic agents, further enhancing toxicity to targeted cells. See, for example, U.S. Pat. No. 5,872,223, hereby incorporated by reference. Such agents, including various bacterial toxins (e.g., *Pseudomonas* exotoxin), ricin A-chain, daunorubicin, methotrexate, and ribosome inhibitors (e.g., trichosantin). Also, the antibodies of this invention may be labeled with alpha, beta, or Auger electron emitters, resulting in immunoconjugates for targeted radiotherapy.

Thus, EphA2-specific antibodies may be used in a variety of methods and compositions for detecting and treating metastatic disease.

EXAMPLE 1

Characterization of EphA2 Expression in Metastatic Cells

Figure 2A:
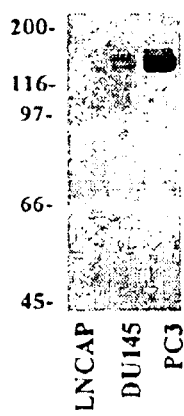
FIGS. 2A–C show a series of western blots showing EphA2 expression in human cell lines.
Figure 2B:
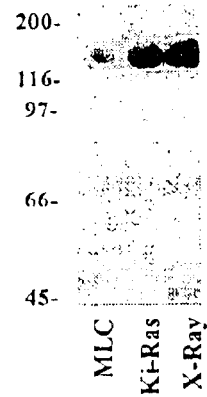
Figure 2C:
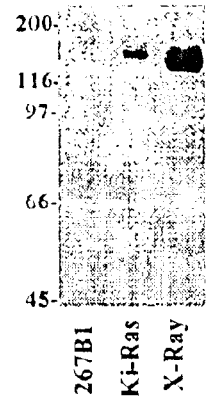
Figure 3:
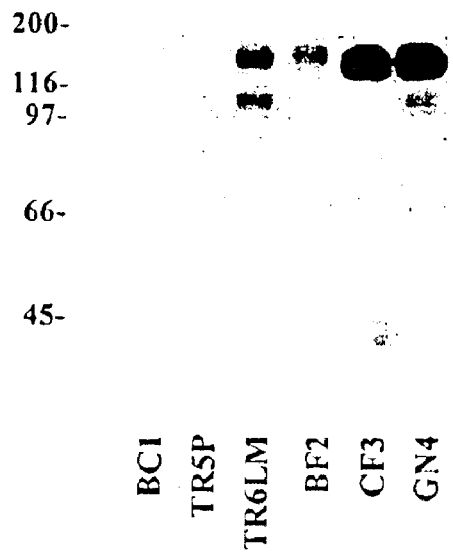
FIG. 3 is similar to FIG. 2, except showing EphA2 expression in canine prostatic cancer cells.

Following the RIMMS strategy using tyrosine phosphorylated proteins from Ras-transformed human epithelial cells, hybridomas were screened, and an antibody specific for EphA2 has been isolated. This antibody, B2D6, was used to assess the levels of EphA2 expression in nontransformed prostatic epithelial cells and prostatic tumor cells. Low levels of EphA2 expression were found in non-transformed prostatic epithelial cells, but this EphA2 expression was enriched within sites of cell-cell contact and interacted with cell-bound ligand. Compared to non-transformed cells, two features distinguish EphA2 in metastatic prostate cancer cells: 1) EphA2 is overexpressed; 2) EphA2 is diffusely distributed and does not appear to interact with ligand. To confirm these data, western blots were performed using the EphA2 specific antibodies. EphA2 overexpression in human prostate cancer cells (LNCAP, DU145, PC3) directly correlates with their invasiveness in vitro and in vivo. Of the three lines tested, LNCAP is the least aggressive, DU145 is more aggressive, and PC3 is the most aggressive. As seen in FIG. 2, DU145 cells exhibit higher levels of EphA2 expression than LNCAP, and PC3 cells exhibit even higher levels of EphA2 expression. Similarly, as shown in FIGS. 2B and 2C, EphA2 expression is elevated in variants of human prostatic epithelial cells transformed by oncogenic K-Ras or X-irradiation. The three lanes in FIG. 2B show "normal" MCL prostatic epithelial cells, and K-Ras and X-ray transformed cell lines derived therefrom. Similarly, the three lanes of FIG. 2C show "normal" 267B1 prostatic epithelial cells, and K-Ras and X-ray transformed cell lines derived therefrom. As seen in FIGS. 2B and 2C, the transformed cells all exhibited elevated EphA2 levels. FIG. 3 shows similar western blots, except using prostate cancer cell lines from dogs. As shown in FIG. 3, consistent with the results from human cells, EphA2 is overexpressed in metastatic prostatic carcinoma cells derived from dogs with spontaneous prostate cancer.

The metastatic prostate cell lines can be subdivided into three categories: 1) cells derived from primary prostate tumors; 2) cells derived from metastases that are poorly metastatic in vivo; 3) cells derived from metastases that are highly metastatic in vivo. The western blots using EphA2-specific antibodies have revealed that EphA2 expression is elevated in all cells derived from metastases, with highest EphA2 expression in cells that retain metastatic potential in vivo (as assessed using athymic mouse models). Interestingly, B2D6 studies have shown that EphA2 is overexpressed in cells from prostate cancer metastases compared to lines established from the primary tumor of same patient. Taken together, these results all reveal EphA2 overexpression in metastatic prostate tumor cells.

Similar EphA2 expression patterns have been found with breast cancer cells. In normal mammary epithelial cells, EphA2 is enriched within the cell—cell junctions. By contrast, non-metastatic breast cancer cells do not express EphA2, while metastatic breast cancer cells overexpress EphA2. In metastatic breast cancer cells, EphA2 is redistributed into the membrane ruffles and, thus, is available for antibody binding.

EXAMPLE 2

In Vitro Targeting of Metastatic Cells

EphA2 overexpression renders metastatic cells susceptible to antibody-mediated selected killing with the present antibodies specific for an extracellular epitope of EphA2. While normal cells express EphA2, it is believed that ligand binding or clustering within sites of cell-cell contact occludes extracellular epitopes in normal cells and renders them inaccessible to antibodies specific for an extracellular epitope of EphA2. The tumor selectivity of the antibodies of the present invention is believed to rival or exceed that of Herceptin® for targeting metastatic cancer.

EphA2 overexpression provides a basis for targeting metastatic cancer cells with EphA2-specific antibodies. Antibodies specific for an extracellular epitope of EphA2, such as those produced by hybridoma B2D6, may be used to alter selectively (versus normal cells) the proliferative or invasive behaviors of metastatic cancer cells. In both metastasis-derived and laboratory-induced transformation, EphA2 overexpression correlates with invasiveness, whereas non-invasive cells have lower levels of EphA2 expression.

To measure the effect of B2D6 on cell growth, cells are incubated with purified B2D6, and cell proliferation is measured by counting cells microscopically (using a hemacytometer) and by measuring DNA synthesis. For example, normal growth media is supplemented with B2D6 and BrdU, and BrdU incorporation is measured over the following four hours. To measure the effects of B2D6 over longer times, samples are counted at 24 hour intervals, with BrdU added to the culture media for the final four hours of incubation. As a third measure of cell growth, the effect of B2D6 on the growth of metastatic cells in soft agar is determined. Soft agar plating assays are used, wherein $2 \times 10^4$ metastatic cells are plated atop agar, in the presence or absence of B2D6 (0–10 nM), and colony growth is evaluated at three-day intervals thereafter.

It is believed that B2D6 decreases the growth of metastatic cells. Preliminary results reveal that B2D6 aggregates EphA2 and blocks about 50% of growth of metastatic breast cancer cells (which also overexpress EphA2) over the first four hours of incubation. Although EphA2 is not tyrosine phosphorylated in metastatic breast cancer cells, tyrosine phosphorylation is restored in these B2D6 treated cells. Thus, B2D6 is believed to restore normal EphA2 function.

Additional studies with prostate cancer cells are being performed to determine if longer incubations with B2D6 further inhibit metastatic cell growth. Non-transformed epithelial cells express some EphA2, albeit much less than metastatic cells, and some toxicity to non-transformed cells is possible. The minimum effective and maximum non-toxic dosage levels of antibodies in accordance with one aspect of this invention can be identified by routine experimentation, but preferably, typical doses will range from about 0.1 to about 20 mg/kg of patient body weight. The preferred dose will depend on many parameters, including the nature of the tumor, patient history, patient condition, the possible co-use of other oncolytic agents, and methods of administration. Antibody levels that-best discriminate between normal and metastatic cells will be used in treatment of metastatic tumors overexpressing EphA2 proteins.

EXAMPLE 3

In Vitro Antibody Mediated Cytotoxicity

Preliminary results demonstrate that EphA2 antibodies impede metastatic cell growth. To measure antibody-directed cytotoxicity, preferably, nonradioactive versions of $^{51}$Cr-release assays using target cells (normal or metastatic prostatic epithelial cells) labeled with europium chloride (EuCl$_3$) and diethylenetriamine-pentaacetic acid (DTPA) are performed. After washing away unincorporated Eu$^{3+}$, naphthoyltrifluoroacetone (NTA) and trioctylphosphine oxide are incubated with the cytolytic agents and assay supernatants. The luminescence of resultant ternary complex (Eu$^{3+}$/NTA/trioctylphosphine oxide) is measured using a fluorescence microplate reader. The sensitivity of this Eu$^{3+}$-release assay for complement-mediated cytolysis has been reported to be fivefold better than $^{51}$Cr-release assays. To determine specific lysis, parallel samples are hyponically lysed by adding distilled water. Untreated samples and isotype matched antibodies serve as negative controls.

To model complement-mediated death in vitro, cells are labeled with B2D6 and exposed to sera that has not been heat-inactivated. For antibody dependent cellular cytotoxicity ("ADCC"), both control and B2D6-treated prostate cells are incubated with peripheral blood mononuclear cells (PBMC; 10:1 E/T ratio).

It is believed that complement and ADCC both promote specific killing of the metastases. Antibody dose can be varied in order to establish LD$_{50}$ measurements for metastatic and normal cells. Antibody concentrations that maximize specific killing of metastatic cells (PC3, 267-Ras, 267-X) while minimizing the death to non-transformed prostatic epithelia (267, MLC) are determined by routine experimentation. Also, ADCC can be combined with complement to further enhance tumor killing by treating the samples with tumor necrosis factor (TNF). There is evidence that TNF potentiates the killing of tumor cells by EGFR and Her2-specific antibodies. It is expected that humanizing the antibodies of this invention would provide for better complement or ADCC results.

It is believed that B2D6 kills tumor cells through complement cascade or ADCC. However, covalent or non-covalent conjugation of the present antibodies to art-recognized cytotoxic agents can further enhance toxicity to targeted cells. Examples of toxins appropriate for immunoconjugation include *Pseudomonas* exotoxin or ricin A-chain.

EXAMPLE 4

In Vivo Targeting of Metastatic Cells

The present EphA2 antibodies, particularly those produced by hybridoma B2D6, are effective in blocking the growth and invasiveness of prostate cancer cells in vivo. The efficacy of B2D6 in blocking the growth of primary prostate tumors using subcutaneous implantation of PC3 tumor cells in mice is determined by use of subcutaneous models. The primary advantages of subcutaneous models are the ease of implantation and subsequent monitoring of tumor size. $5 \times 10^5$ PC3 cells are inoculated subcutaneously into the right craniolateral thorax (axilla) using aseptic technique. Tumors are measured every 34 days using vernier calipers until they reach a volume of 0.2–0.3 cm$^3$. At that time, the mice are divided into four groups (8–10 animals each): Group 1 (vehicle control), Groups 2–4 are treated with 0.1, 1.0, or 10 mg/kg B2D6, administered intraperitoneally, twice a week. The mice are then monitored every 3 days to measure tumor volume (with vernier calipers), body weight, and life span. After no greater than 60 days past implantation, the animals are sacrificed and postmortem evaluations of tumorigenesis, including measurement and weight of implanted tumors and proximal lymph nodes, macroscopic evaluation of soft tissues for tumors (lymph nodes and lung), and formalin fixation of the primary tumor and tissues, are performed. The tissues are evaluated by immunohistochemistry using D7 (another EphA2 specific antibody that is amenable to immunohistochemistry) to determine the level of EphA2 expression in the tumors. In particular, tumor cells that escape B2D6 treatment are studied to determine whether they have low levels of EphA2 expression. Also, EphA2 expression in the individual animals is correlated with tumor invasiveness.

As target-negative controls for specificity, parallel studies are performed using DU145 cells, which express very low levels of EphA2. Whereas the growth of PC3 tumors are believed to be sensitive to B2D6, tumors caused by DU145 are believed be insensitive. Statistical significance of B2D6 inhibition of tumorigenicity, overall metastatic frequency, and frequency of distant metastases is tested using computerized statistical packages (PC/SAS Ver. 6.04), with differences considered significant if $p<0.05$.

While subcutaneous implantation is a popular and valuable method for modeling tumor cell growth, differences between the microenvironment of the skin and prostate can cause rather dramatic differences in cell behavior. For example, PC3 cells rarely metastasize when implanted subcutaneously whereas intraprostatic implantation (orthotopic) facilitates metastasis. Thus, PC3 cells are implanted in the prostate by exposing the prostate via laparotomy and inoculating tumor cells into prostate gland using a surgical microscope. After seven days, the mice begin receiving treatment with B2D6, as described above, and the animals are sacrificed no later than 60 days after implantation (or if the animals become moribund). The tumors are palpated at 3–5 day intervals, at which time data on tumor size, animal weight, and survival are collected. Post-mortem evaluations are also performed as described above, with emphasis upon the effect of B2D6 upon metastatic potential (to lungs and regional lymph nodes). B2D6 is believed to block the primary tumor and metastatic potential of PC3 cells in a dose-dependent manner.

To minimize identification of strain or clonal-specific effects, identical analyses using other model systems can be employed. For example, the effects of B2D6 on the growth or metastasis of tumors caused by implantation of K-Ras or X-ray transformed 267B1 can be compared to the effects on MLC human prostatic by epithelial cell lines.

EXAMPLE 5

Development of "Second Generation" EphA2-Based Antibody Therapeutics

While EphA2 overexpression in metastatic prostate cancer cells provides a degree of selectivity comparable to Herceptin® in breast cancer, unique properties of EphA2 are believed to allow for even more selective targeting. In particular, EphA2 at the surface of non-transformed epithelia is tightly packed into cell-cell contacts whereas EphA2 on metastatic cells is diffusely distributed. It is thus likely that some epitopes on EphA2 are accessible in metastases but protected by ligand in normal prostatic epithelia. The EphA2 antibodies that provide the optimal discrimination between normal and metastatic prostatic epithelia are selected.

Figure 4:
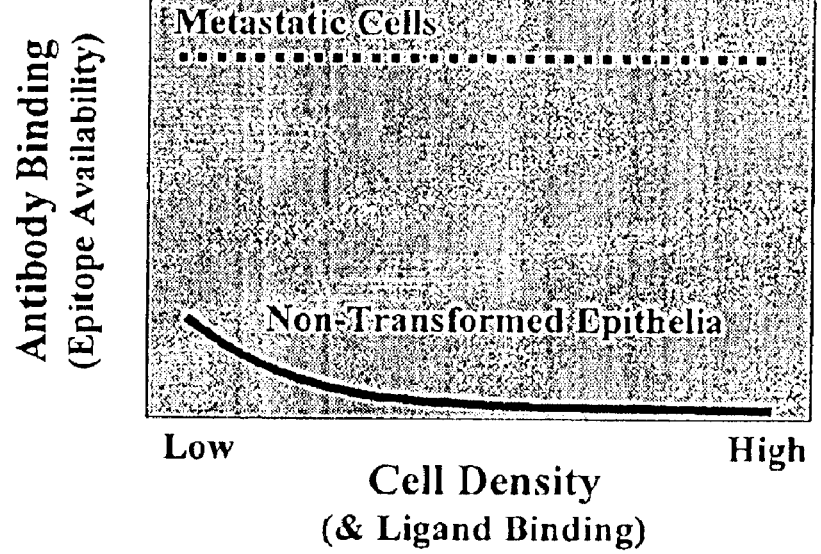
FIG. 4 shows predicted antibody binding plotted against cell density in a screening procedure for antibodies which are specific for an extracellular epitope of EphA2.

The panel of antibodies generated previously are screened for epitopes on EphA2 that are found at the cell surface. Using flow cytometry, EphA2 expression in a variety of "normal" (e.g., 267B or MLC cells) and metastatic cells (PC3 cells) are compared. For example, confluent monolayers of normal and metastatic cells are labeled with B2D6. To insure that antibodies are selected that are specific for epitopes inaccessible in normal cells but accessible in metastatic cells, antibodies are selected whose binding decreases in normal cells with increasing cell density but whose binding remains constant in metastatic cells, as shown in FIG. 4. After labeling with fluorescein-secondary antibodies, EphA2 expression is evaluated by using flow cytometry. The antibodies that best distinguish between normal and metastatic cells are selected. Specificity for EphA2 is confirmed via western blotting and immunoprecipitation studies. Antibodies exhibiting the best selectivity are then humanized using art recognized techniques.

EXAMPLE 6

Altered EphA2 Expression Through Transfection

To assess the consequences of EphA2 overexpression, MCF-10A cells were transfected with human EphA2 cDNA (EphA2) or a vector control (vector). After establishing cultures of MCF-10A cells with stable overexpression of EphA2, microscopic evaluation revealed differences in the cell morphology as compared to vector-transfected control cells (not shown). Non-transformed MCF-10A cells display an epithelial morphology and interact with one-another, even at low cell density. In contrast, EphA2-overexpressing MCF-10A cells (MCF$^{EphA2}$) adopt a fibroblast-like morphology and do not form cell-cell contacts, even at high cell density. To confirm that the mesenchymal morphology does not represent clonal variation, a separate sample of MCF-10A cells transfected with EphA2 cDNAs yielded identical results.

Cell-ECM adhesions were evaluated by incubating cells on ECM at 37° C. for 30 minutes before vigorous washing to remove weakly adherent cells. These assays revealed a 24-fold increase in ECM attachments in MCF$^{EphA2}$ cells relative to vector-transfected controls ($P<4\times10^{-4}$). Cell-cell adhesions were assayed by incubating cells in suspension and counting the average size of cell colonies. Whereas vector-transfected MCF-10A cells interact with one-another in colonies with an average size of 4.1 cells, the average colony size of MCF$^{EphA2}$ cells is reduced to 1.3 cells ($P<3\times10^{-5}$).

Since stable cell-cell contacts cause EphA2 to become enriched within sites of cell-cell contact, EphA2 subcellular localization was assessed by immunostaining with specific antibodies. The EphA2 on non-transformed MCF-10A cells was restricted to a narrow line where adjacent cells came into direct contact, with little staining of membrane that was not in contact with neighboring cells. In contrast, the pattern of EphA2 staining on MCF$^{EphA2}$ cells was diffuse, with little staining of cell-cell contacts.

The lack of EphA2 within cell-cell contacts in MCF$^{EphA2}$ cells was intriguing since EphA2 is stimulated by ligands that are anchored to the cell membrane. To measure EphA2 stimulation, the phosphotyrosine content of immunoprecipitated EphA2 was measured by Western blot analysis with phosphotyrosine specific antibodies. Whereas the EphA2 in vector-transfected MCF 10 cells was tyrosine phosphorylated, EphA2 was not tyrosine phosphorylated in MCF$^{EphA2}$ cells. The decreased phosphotyrosine content was confirmed using multiple EphA2 antibodies for immunoprecipitation (D7, B2D6) and different phosphotyrosine-specific antibodies (4G 10, PY20) for Western blot analyses.

EXAMPLE 7

Malignancy and Metastasis Through EphA2 Transfection

Malignant transformation was studied in vitro, and MCF$^{EphA2}$ cells were found to colonize soft agar. Whereas vector-transfected MCF-10A cells formed 0.3 colonies per high-power field, while MCF$^{EphA2}$ cells displayed increased colony growth in soft agar, with an average of 3.0 colonies per high-power field ($P<3\times10^{-7}$). Vector and EphA2 overexpressing MCF-10A cells were allowed to interact with Matrigel (Collaborative, Bedford, Mass.). Non-transformed MCF-10A cells rapidly organized into spherical colonies when cultured on Matrigel whereas MCF$^{EphA2}$ cells adopted a stellate organization that was indistinguishable from the behavior of metastatic cells (e.g., MDA-MB-231, MDA-MB,435).

Since in vitro analyses of transformation do not always predict tumorigenic potential in vivo, control or EphA2-overexpressing MCF-10A cells were implanted into athymic (nu/nu) mice. Subcutaneous injection of MCF$^{EphA2}$ cells caused the formation of palpable tumors within four days in 19 of 19 mice. The median volume of resulting tumors related to the number of implanted cells and reached an average of 300 mm$^3$ (for samples injected with $5\times10^6$ cells) within 10 days (Table I). Necropsy revealed that the tumors were firmly attached to the underlying axillary muscle and surrounded by fibrous tissue. Histologically, the neoplastic cells were invasive and associated with fibrous connective tissue. These neoplastic cells exhibited moderate cytoplasmic and nuclear pleiomorphism and formed dysplastic tubular and secreting structures. In control experiments, cells transfected with vector DNA failed to grow in athymic mice (O of 13; Table I) and necropsy failed to identify any growth or invasion of these cells.

Since the highest levels of EphA2 were consistently found in breast cancer cells that are metastatic in vivo, $1\times10^6$ control or MCF$^{EphA2}$ cells were injected into the tail vein of athymic mice. Within seven days, necropsy revealed lung micrometastases within large vessels in 2 of 4 mice injected with MCF$^{EphA2}$ cells (Table I). The metastases were generally found to occlude large blood vessels but did not breach the vessel wall. Immunohistochemical staining with cytokeratin antibodies confirmed the epithelial nature of the thrombus and a lack of anti-thrombin staining revealed that the thrombus did not represent an abnormal or atypical outgrowth of endothelial cells. No lung colonization was observed in mice that had been injected with control MCF-10A cells (Table I).

TABLE I

Tumorigenic and Metastatic Potential of EphA2-Transformed MCF-10A Cells

| Cell | Site of Inoculation | # of Cells Injected | Incidence of Tumorigenicity | Tumor Volume (mm$^3$) |
|---|---|---|---|---|
| Ctrl | Subcutaneous | $1\times10^6$ | 0/9 | N/A |
| EphA2 | | $1\times10^6$ | 9/9 | 66 ± 20 |
| Ctrl | Subcutaneous | $5\times10^6$ | 0/4 | N/A |
| EphA2 | | $5\times10^6$ | 10/10 | 293 ± 70 |
| Ctrl | Tail Vein | $1\times10^6$ | 0/4 | |
| EphA2 | | $1\times10^6$ | 2/4 | |

EXAMPLE 8

Metastatic Targeting Using EphA2 Agonists

To test if EphA2 could be stimulated by an agonist, MCF$^{EphA2}$ cells were suspended in soft agar in the presence or absence of 0.5 mg/mL EphrinA1-F$_c$. EphrinA1-F$_c$ increased the phosphotyrosine content of EphA2, and EphrinA1-F$_c$-treated cells exhibited reduced colony formation in soft agar by 49% relative to vehicle-treated controls ($P<5\times10^{-6}$). To test if EphA2 stimulation could alter cell behavior on Matrigel, the MCF$^{EphA2}$ cells were treated with 0.5 mg/mL EphrinA1-F$_c$, which restored a spherical phenotype that was comparable to nontransformed MCF$^{EphA2}$ cells. Thus, EphA2 stimulation reverses the effects of EphA2 overexpression. Despite its inability to interact with its endogenous ligands, the EphA2 in MCF$^{EphA2}$ cells responded to exogenous stimuli.

Although the invention has been described in detail with reference to preferred embodiments, variations and modifications exist within the scope and spirit of the invention as described and defined in the following claims.

What is claim is:

1. A method for treatment of a patient having a tumor, said tumor comprising a population of tumor cells that express EphA2, said method comprising administering to the patient a therapeutically effective amount of an ephrin comprising the extracellular domain of ephrinA1 that increases the phosphotyrosine content of EphA2, wherein said administration reduces tumor volume.

2. The method of claim 1 wherein the tumor cells overexpress EphA2 as compared to normal cells.

3. The method of claim 1 wherein said administration inhibits proliferation of the tumor cells.

4. The method of claim 1 wherein said administration reduces invasiveness of the tumor cells compared to untreated tumor cells.

5. A method for treatment of a patient having a tumor, said tumor comprising a population of tumor cells that express EphA2, said method comprising administering to the patient a therapeutically effective amount of an ephrin comprising the extracellular domain of ephrinA1 that increases the phosphotyrosine content of EphA2, wherein said administration impedes proliferation of said tumor cells.

6. The method of claim 5 wherein the tumor cells overexpress EphA2 as compared to normal cells.

7. A method for treatment of a patient having a tumor, said tumor comprising a population of tumor cells that express EphA2, said method comprising administering to the patient a therapeutically effective amount of an ephrin comprising the extracellular domain of ephrinA1 that increases the phosphotyrosine content of EphA2 in said tumor cells as compared to untreated tumor cells.

8. The method of claim 7 wherein the tumor cells overexpress EphA2 as compared to normal cells.

9. A method for reducing the invasiveness of a cancer cell that expresses EphA2, the method comprising contacting the cancer cell with an ephrin comprising the extracellular domain of ephrinA1 that increases the phosphotyrosine content of EphA2, thereby reducing the invasiveness of the cancer cell compared to an untreated cancer cell.

10. The method of claim 9 wherein the cancer cell overexpresses EphA2 as compared to a normal cell.

11. The method of claim 9 wherein the cancer cell is present in a mammalian patient.

12. A method for reducing the proliferative behavior of a cancer cell that expresses EphA2, the method comprising contacting the cancer cell with an ephrin comprising the extracellular domain of ephrinA1 that increases the phosphotyrosine content of EphA2, thereby reducing the proliferative behavior of said cancer cell compared to an untreated cancer cell.

13. The method of claim 12 wherein the cancer cell overexpresses EphA2 as compared to a normal cell.

14. The method of claim 12 wherein the cancer cell is present in a mammalian patient.

15. A method for treatment of a patient having a tumor, said tumor comprising a population of tumor cells that express EphA2, said method comprising administering to the patient a therapeutically effective amount of an anti-EphA2 antibody that increases the phosphotyrosine content of EphA2, wherein said administration reduces tumor volume.

16. The method of claim 15 wherein the tumor cells overexpress EphA2 as compared to normal cells.

17. The method of claim 15 wherein said administration inhibits proliferation of the tumor cells.

18. The method of claim 15 wherein said administration reduces invasiveness of the tumor cells compared to untreated tumor cells.

19. The method of claim 15 wherein the anti-EphA2 antibody is a monoclonal antibody.

20. The method of claim 19 wherein the monoclonal antibody is humanized.

21. The method of claim 19 wherein the monoclonal antibody is conjugated to a cytotoxic agent.

22. A method for treatment of a patient having a tumor, said tumor comprising a population of tumor cells that express EphA2, said method comprising administering to the patient a therapeutically effective amount of an anti-EphA2 antibody that increases the phosphotyrosine content of EphA2, wherein said administration impedes proliferation of said tumor cells.

23. The method of claim 22 wherein the cells overexpress EphA2 as compared to normal cells.

24. The method of claim 22 wherein the anti-EphA2 antibody is a monoclonal antibody.

25. The method of claim 24 wherein the monoclonal antibody is humanized.

26. The method of claim 24 wherein the monoclonal antibody is conjugated to a cytotoxic agent.

27. A method for treatment of a patient having a tumor, said tumor comprising a population of tumor cells that express EphA2, said method comprising administering to the patient a therapeutically effective amount of an anti-EphA2 antibody that increases the phosphotyrosine content of EphA2 in said tumor cells as compared to untreated tumor cells.

28. The method of claim 27 wherein the tumor cells overexpress EphA2 as compared to normal cells.

29. The method of claim 27 wherein the anti-EphA2 antibody is a monoclonal antibody.

30. The method of claim 29 wherein the monoclonal antibody is humanized.

31. The method of claim 29 wherein the monoclonal antibody is conjugated to a cytotoxic agent.

32. A method for reducing the invasiveness of a cancer cell that expresses EphA2, the method comprising contacting the cancer cell with an anti-EphA2 antibody that increases the phosphotyrosine content of EphA2, thereby reducing the invasiveness of the cancer cell compared to an untreated cancer cell.

33. The method of claim 32 wherein the cancer cell overexpresses EphA2 as compared to a normal cell.

34. The method of claim 32 wherein the cancer cell is present in a mammalian patient.

35. The method of claim 32 wherein the anti-EphA2 antibody is a monoclonal antibody.

36. The method of claim 35 wherein the monoclonal antibody is humanized.

37. The method of claim 35 wherein the monoclonal antibody is conjugated to a cytotoxic agent.

38. A method for reducing the proliferative behavior of a cancer cell that expresses EphA2, the method comprising contacting the cancer cell with an anti-EphA2 antibody that increases the phosphotyrosine content of EphA2, thereby reducing the proliferative behavior of said cancer cell compared to an untreated cell.

39. The method of claim 38 wherein the cancer cell overexpresses EphA2 as compared to a normal cell.

40. The method of claim 38 wherein the cancer cell is present in a mammalian patient.

41. The method of claim 40 wherein the anti-EphA2 antibody is a monoclonal antibody.

42. The method of claim 40 wherein the monoclonal antibody is humanized.

43. The method of claim 40 wherein the monoclonal antibody is conjugated to a cylotoxic agent.

44. The method of any one of claims 1, 5, 7, 17, 22 or 27 wherein the population of tumor cells comprises cells selected from the group consisting of breast cancer cells, prostate cancer cells, lung cancer cells and colon cancer cells.

45. The method of any one of claims 9, 12, 32 or 38 wherein the cancer cell is a cell selected from the group consisting of a breast cancer cell, prostate cancer cell, lung cancer cell and colon cancer cell.

46. The method of any of claims 1, 5, 7, 9 or 12 wherein the ephrin comprises ephrinA1-Fc.

* * * * *

UNITED STATES PATENT AND TRADEMARK OFFICE
CERTIFICATE OF CORRECTION

PATENT NO. : 6,927,203 B1 Page 1 of 1
APPLICATION NO. : 09/640935
DATED : August 9, 2005
INVENTOR(S) : Kinch et al.

It is certified that error appears in the above-identified patent and that said Letters Patent is hereby corrected as shown below:

Title page, Item [54] and Column 1, line 1,
Title, delete "TREATMENT OF METASTATIC DISEASE" and insert
-- EPHA2 AS A THERAPEUTIC TARGET FOR CANCER --.

Title page,
Item [56], References Cited, OTHER PUBLICATIONS,
"Hess et al.," reference, delete "2001; 61-3250-3255" and insert -- 2001;61:3250-3255 --.
"Jakobovits et al.," reference, delete "humid-derived" and insert -- human-derived --.
"Khosravi-Far et al." reference, delete "15(1)" and insert -- *15*(11) --.
"O'Brien et al.," reference, delete "dephsphorylation" and insert -- dephosphorylation --.
Delete "Ogawa et al. The ephrin—A1 ligand and its receptor. EphA2, are expressed during tumor neovascularization." *Oncogene*. 2000; *19*(52):6043-52. Dec. 7." and insert -- Ogawa et al. "The ephrin—A1 ligand and its receptor, EphA2, are expressed during tumor neovascularization." *Oncogene*. 2000; *19*(52):6043-52. --.

Column 8,
Line 66, delete "34" and insert -- 3-4 --.

Column 12,
Line 28, delete "MCF$^{EphA2}$" and insert -- MCF-10A --.

Signed and Sealed this

Twenty-seventh Day of June, 2006

JON W. DUDAS
*Director of the United States Patent and Trademark Office*